United States Patent [19]

Lucey

[11] Patent Number: 6,042,573

[45] Date of Patent: Mar. 28, 2000

[54] SURGICAL VALVE

[75] Inventor: Paul V. Lucey, Salem, N.H.

[73] Assignee: Smith & Nephew, Inc., Memphis, Tenn.

[21] Appl. No.: 08/990,572

[22] Filed: Dec. 11, 1997

[51] Int. Cl.$^7$ .................................................. A61M 5/00
[52] U.S. Cl. ........................... 604/246; 604/26; 604/256; 604/23; 606/213
[58] Field of Search ................................ 606/1, 185, 213; 604/23, 26, 246, 247, 256, 27, 30, 31, 34, 35, 73, 93, 174, 175, 278

[56] References Cited

U.S. PATENT DOCUMENTS

| | | | |
|---|---|---|---|
| 5,299,582 | 4/1994 | Potts | 128/846 |
| 5,328,458 | 7/1994 | Sekino et al. | 604/23 |
| 5,336,193 | 8/1994 | Rom et al. | 604/171 |
| 5,366,478 | 11/1994 | Brinkerhoff et al. | 660/213 |
| 5,423,741 | 6/1995 | Frank | 604/26 |
| 5,437,683 | 8/1995 | Neumann et al. | 606/151 |
| 5,441,486 | 8/1995 | Yoon | 604/167 |
| 5,480,410 | 1/1996 | Cuschieri et al. | 606/213 |
| 5,514,133 | 5/1996 | Golub et al. | 606/1 |
| 5,524,644 | 6/1996 | Crook | 128/888 |
| 5,526,536 | 6/1996 | Cartmill | 2/161.7 |
| 5,545,179 | 8/1996 | Williamson, IV | 606/213 |
| 5,549,546 | 8/1996 | Schneider et al. | 604/26 |
| 5,634,911 | 6/1997 | Hermann et al. | 604/256 |
| 5,634,937 | 6/1997 | Mollenauer et al. | 606/213 |
| 5,636,645 | 6/1997 | Ou | 128/898 |
| 5,640,977 | 6/1997 | Leahy et al. | 128/897 |
| 5,653,705 | 8/1997 | de la Torre et al. | 606/1 |
| 5,800,381 | 9/1998 | Ognier | 604/26 |
| 5,871,474 | 2/1999 | Hermann et al. | 604/256 |

FOREIGN PATENT DOCUMENTS

| | | |
|---|---|---|
| 0 807 416 A2 | 11/1997 | European Pat. Off. . |
| WO 95/07056 | 3/1995 | WIPO . |
| WO 95/22289 | 8/1995 | WIPO . |
| WO 95/27445 | 10/1995 | WIPO . |
| WO 95/27468 | 10/1995 | WIPO . |
| WO 96/10963 | 4/1996 | WIPO . |
| WO 97/11642 | 4/1997 | WIPO . |

OTHER PUBLICATIONS

Gorey et al., "Video–assisted Nissen's fundoplication using a hand–access port", *Min. Invas. Ther. & Allied Technol.*, 5:364–366, (1996).

*Primary Examiner*—Wynn Wood Coggins
*Assistant Examiner*—Deborah Blyveis
*Attorney, Agent, or Firm*—Fish & Richardson P.C.

[57] ABSTRACT

In a laparoscopic surgery or the like, access is provided to an opening in a body cavity that contains insufflation gas at an insufflation pressure. The flow of insufflation gas from the body cavity through the opening is limited in response to the sensed insufflation pressure in the cavity.

17 Claims, 6 Drawing Sheets

SURGICAL VALVE

BACKGROUND OF THE INVENTION

The invention relates to methods and apparatus for providing access to a body cavity of a patient during surgery.

In some forms of surgery, such as laparoscopy, a surgeon operates on a patient through one or more incisions that provide access to a patient's body cavity. The surgeon inserts through the incisions one or a combination of surgical implements, including visual aid devices such as a laparoscope or endoscope, the surgeon's hand or hands, and surgical instruments for, e.g., grasping, cutting, or grinding tissue. The body cavity is inflated with an insufflation gas to facilitate access to one or more organs or surgical sites.

SUMMARY OF THE INVENTION

In one aspect of the invention, an apparatus including a controllable valve provides access to an opening in a body cavity containing insufflation gas at an insufflation pressure. A controller responsive to a pressure sensor output signal corresponding to the insufflation pressure provides an actuation signal, to which the controllable valve responds to restrict flow of insufflation gas from the body cavity through the opening.

Embodiments of this aspect of the invention can include one or more of the following features. The controllable valve, which can include an inflatable annular bladder sized to fit within the opening, is actuated to restrict flow (e.g., by inflating the bladder) when the insufflation pressure is below a desired level. The bladder can have a conical shape, with the smaller end arranged closer to the opening in the body cavity than the larger end, and can also be segmented. The controllable valve can be an iris valve. The output signal from the sensor can be an electrical signal, or can be a mechanical signal provided by, e.g., an arm, lever, or diaphragm that moves in response to insufflation pressure.

In another aspect of the invention, a system for providing access to a body opening in a body cavity containing insufflation gas includes an inflatable annular bladder. The body opening can be accessed through the central opening defined by the annular bladder. In response to a pressure sensor output signal corresponding to the insufflation pressure, a controller controls a source of pressurized gas to provide pressurized gas to the bladder chamber.

Embodiments of this aspect of the invention can include one or more of the following features. The controller controls the source of pressurized gas to provide pressurized gas to the bladder chamber when the insufflation pressure is below a predetermined level (e.g., as indicated by a sensor in fluid communication with the chamber). No pressurized gas is provided to the bladder when the insufflation pressure is above the predetermined level.

Another source of pressurized gas is also in selective fluid communication with the body cavity. The controller can control this source of gas to provide pressurized gas to the body cavity when the insufflation pressure is below the predetermined level, and to not provide pressurized gas to the body cavity when the insufflation pressure is above the predetermined level.

In another aspect of the invention, access is provided to an opening in a body cavity that contains insufflation gas at an insufflation pressure. The flow of insufflation gas from the body cavity through the opening is limited in response to the sensed insufflation pressure being below a predetermined level.

Embodiments of this aspect of the invention can include one or more of the following features. Flow of insufflation gas from the body cavity through the opening can be limited by inflating an inflatable annular bladder in a tube positioned in or around the opening, e.g., to a pressure that is a function of the insufflation pressure. The bladder is inflated, and insufflation gas is supplied to the body cavity, when the sensed insufflation pressure is below the predetermined level. The bladder is at least partially deflated when the sensed insufflation pressure is above the predetermined level. In this deflated or partially deflated state, the bladder can passively limit the flow of insufflation gas from the body cavity through the opening.

In another aspect of the invention, an apparatus for providing access to a body opening in a body cavity containing insufflation gas includes an inflatable bladder carried in a housing. The housing has opposed open ends and a passageway through which one or more surgical implements can be inserted. The bladder fits inside the housing and is configured to receive fluid at a pressure that is a function of the insufflation pressure.

Embodiments of this aspect of the invention can include one or more of the following features. The bladder can be conical, annular, segmented, or sized to fit within the body opening.

The invention provides a variety of advantages, including guarding against the loss of insufflation pressure in the body cavity during laparoscopic surgery or the like. The valve can be operated in accordance with the insufflation pressure. The valve need not be fully "open" or fully "closed," but rather can be operated over a range of values in accordance with insufflation pressure to reduce the degree to which the valve limits the surgeon's ability to access the body cavity. Insufflation pressure may be maintained even when implements are inserted and removed from the valve at relatively high frequency.

Other advantages and features will become apparent from the following description, as well as from the claims.

DESCRIPTION OF THE PREFERRED EMBODIMENTS

Figure 1:
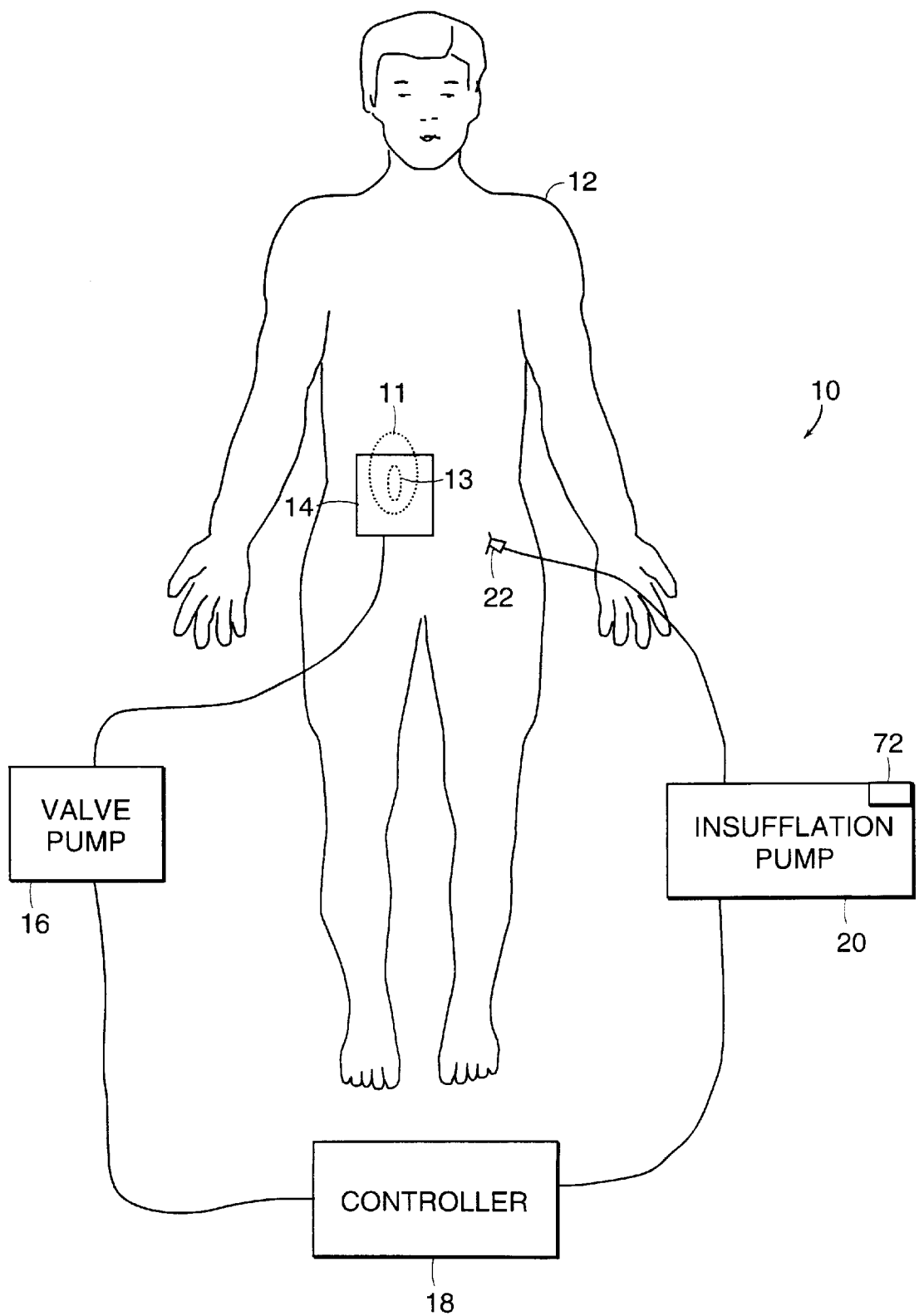
FIG. 1 is a schematic view of an insufflation system.

As shown in FIG. 1, an insufflation system 10 is used to insufflate a body cavity 11 in the area of an incision 13 in a patient 12. The system 10 includes a valve assembly 14, a valve pump 16, a controller 18, an insufflation pump 20, and an insufflation needle 22. The controller 18 controls the valve pump 16 to provide pressurized air to the valve assembly 14, as described in detail below. The controller 18 also controls the insufflation pump 20 to regulate the insufflation pressure in the body cavity 11. The insufflation pump 20 (e.g., a Dyonic Laparoscopic Insufflator Model No. 7205362) can supply pressures sufficient to insufflate the body cavity 11. For example, the insufflation pump 20 can inflate the body cavity 11 to approximately 50 mm Hg (2 in. Hg), while a typical insufflation pressure is 15 mm Hg (0.6 in. Hg). A signal representing the insufflation pressure is provided by an insufflation pressure sensor 72 and sent to the controller 18. The controller 18 can be any device capable of sending control signals to control the insufflation pump 20 and the valve pump 16, e.g., a personal computer or a dedicated microprocessor and associated circuitry. Typically, the controller 18 is programmed using software, hardware, firmware, hardwiring, or a combination of any of these. A surgeon can access the body cavity 11 through the valve assembly 14, e.g., to insert an implement into the cavity.

Figure 2:
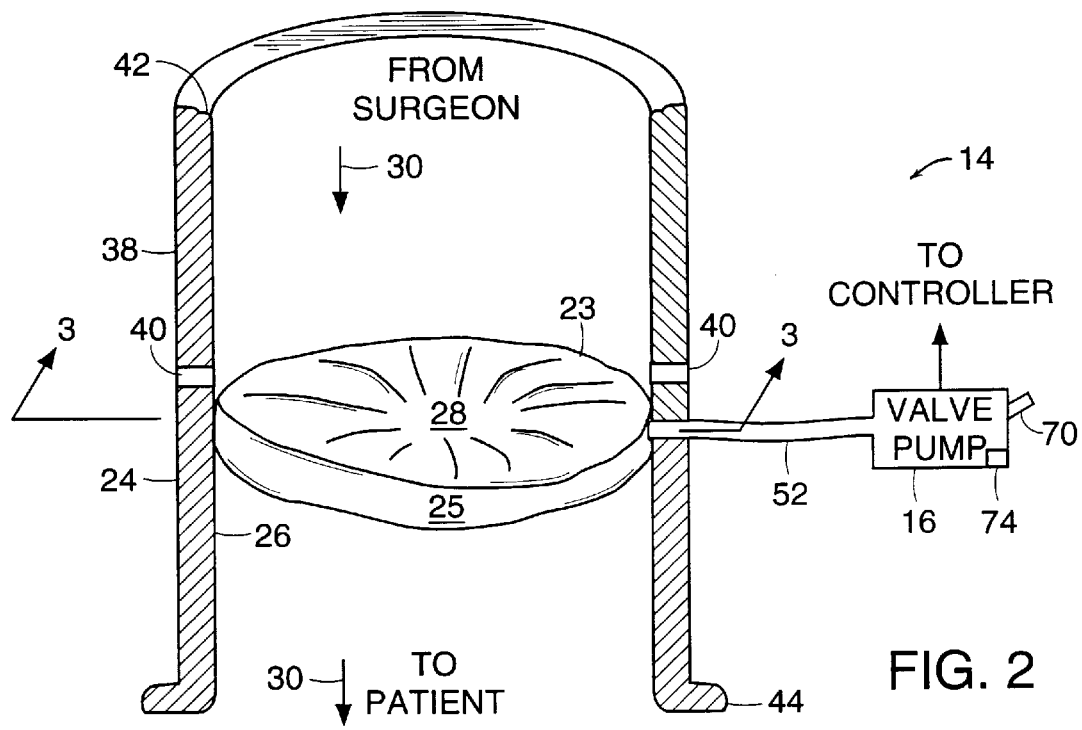
FIG. 2 is a partially cross-sectional view of a valve assembly for use in the system shown in FIG. 1.

As shown in FIG. 2, the valve assembly 14 includes a bladder 23 carried in a rigid tube 24 attached to a sleeve 38. The sleeve 38 is flexible and sized to fit over the surgeon's forearm. The proximal end 42 of the sleeve 38 includes, for example, a hook and loop fastener strap that can be secured around the surgeon's arm to guard against loss of insufflation gas. The sleeve 38 connects to a sleeve coupling 40 that releasably connects to the tube 24 using a releasable coupling such as disclosed in U.S. Pat. No. 5,653,705 (issued Aug. 5, 1997 to De La Torre) incorporated by reference herein. A circular inside surface 26 of the tube 24 forms a seal, preferably air-tight, with an outer perimeter 25 of the bladder 23. The bladder 23 fits snugly within, and is bonded to, the tube 24. The bladder 23 can be sealed to the tube 24 by, e.g., an adhesive, heat welding, or inflating the bladder 23 to expand and conform it to the inside surface 26 of the tube 24 with an interference fit. Also, the bladder 23 can be carried by a rigid or semi-rigid member that is slid into the tube 24 and mounted at an appropriate location. The bladder-and-member assembly can be removed, e.g., for replacement when it becomes worn or soiled.

The tube 24 is sized to allow access to the body cavity 11 (FIG. 1) through an opening 28 defined by the bladder 23 along the direction indicated by arrows 30. For example, the tube 24 can be sized to allow insertion of the surgeon's hand and/or forearm through the opening 28, in which case the inside surface 26 can have a diameter on the order of 100 mm (4 in.). For inserting smaller implements such as endoscopes or surgical instruments, the tube can be smaller, e.g., with an inside diameter on the order of 5–10 mm (0.2–0.4 in.).

The tube 24 has a distal section adapted to be mounted to the patient 12. As shown, the distal section includes a flange 44 that can be mounted directly to the patient using an adhesive, by suturing, or by other appropriate means.

The bladder 23 is inflatable, conical and annular. The bladder 23 is preferably flexible enough that an inner surface of the bladder 23 conforms to the periphery of the implement, yet is durable enough to resist puncture or rupture in normal use. For example, the bladder 23 can be made of a flexible polymer, such as polypropylene or latex. The maximum intended operating pressure of the bladder 23 depends on a variety of factors such as the bladder material, the amount that the surgeon needs to manipulate the implement inside the opening 28, and the bladder's shape. The conical shape of the bladder 23 allows it to conform, either actively under control of the controller 18 or passively due to, e.g., the insufflation pressure, to the implement. The conical shape also facilitates insertion of implements through the opening 28, while guarding against the bladder 23 turning upwards, and thus allowing insufflation gas in the body cavity 11 to escape, when the surgeon removes the implement. Either or both the bladder 23 and the implement can be lubricated to facilitate insertion and removal of the implement.

The valve pump 16 (e.g., an ACI Medical Model No. 025.20-12) is connected to the bladder 23 by a valve pump gas line 52. The bladder 23 conforms to the implement as the valve pump pressurizes the bladder 23. The valve pump 16 can pressurize the bladder 23, e.g., up to 200 mm Hg, and can release gas from the bladder 23 to reduce the pressure in the bladder 23 to as low as 0 mm Hg. The pressure in the bladder 23 is monitored by a bladder pressure sensor 74, in the valve pump 16, that sends a signal representative of the bladder pressure to the controller 18. If the bladder pressure exceeds the maximum desired pressure for the bladder 23, then the valve pump 16, either on its own or under direction of the controller, can shut off, reduce output, or provide either or both of a visual or audio warning. The valve pump 16 also has a manual shutoff switch 70. The valve pump 16 can be a multichannel pump as shown in FIG. 3.

Figure 3:
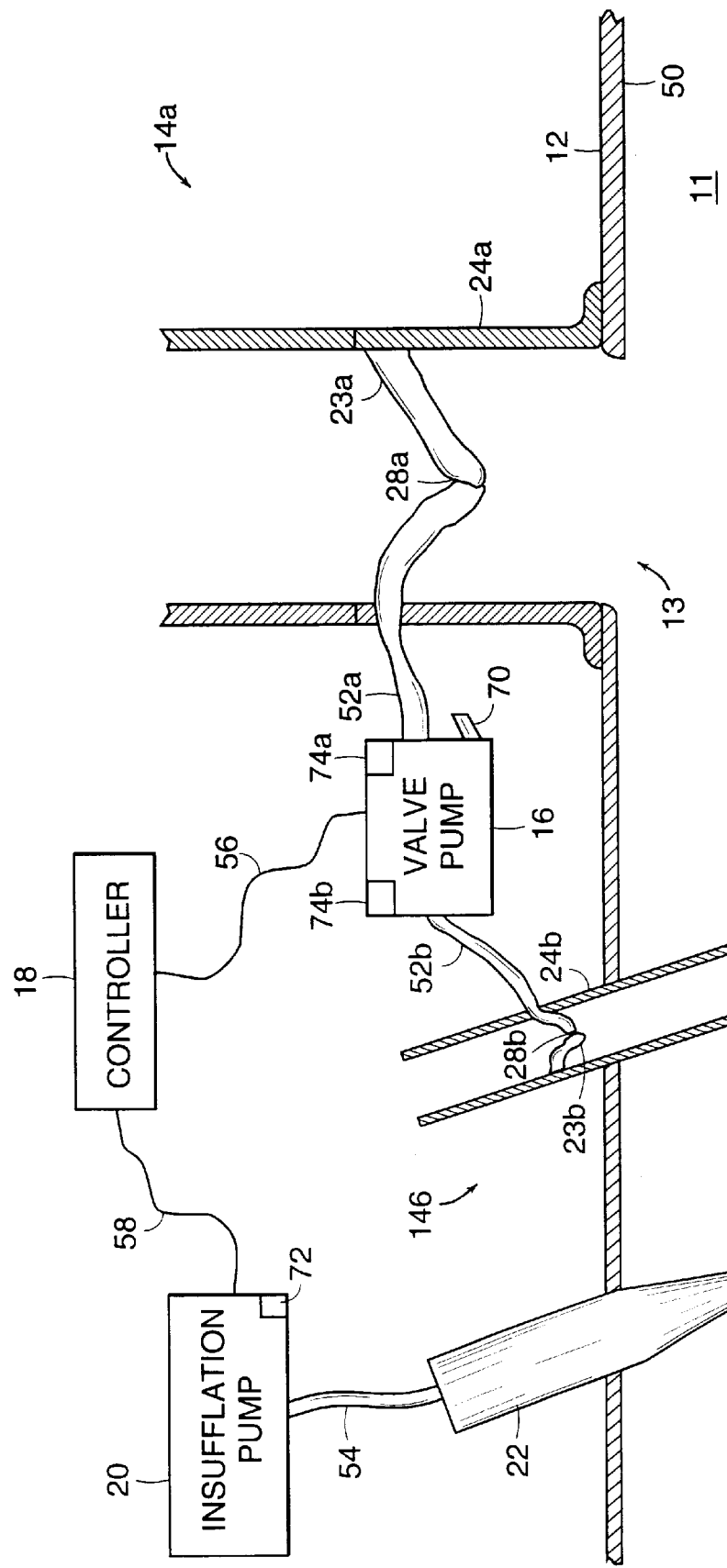
FIG. 3 is a partially cross-sectional detail view of the system shown in FIG. 1.

As shown in FIG. 3, if the valve pump 16 is a multichannel pump (i.e., it can provide multiple independent pressures to, and sense multiple independent pressures in, multiple valves), then two valve assemblies 14a, 14b similar to valve assembly 14 can be used together in a surgical procedure. Alternatively, separate valve pumps 16, one for each valve, can be used. Signals representing bladder pressures are provided by bladder pressure sensors 74a, 74b to the controller 18. The valve 14a is sized for insertion of the surgeon's hand (not shown) and the valve 14b is sized to receive an implement such as a surgical instrument or a visual aid device (not shown).

In a surgical procedure, the valve assemblies 14a, 14b are attached to the patient 12 so that they are sealed in or around the incision 13. For instance, the valve assembly 14a is attached around the incision 13 and the valve assembly 14b is inserted through a body wall 50 of the patient 12 directly into the body cavity 11. The valve pump 16 is connected to the bladders 23a, 23b through respective valve pump gas lines 52a, 52b. The insufflation needle 22 is inserted through the body wall 50, and an insufflation pump gas line 54 connects the insufflation needle 22 to the insufflation pump 20. The valve pump gas lines 52a, 52b. and the insufflation pump gas line 54 are preferably flexible, and made of a material that can withstand the pressures encountered during use. Electrical lines 56 and 58 connect the controller 18 to the valve pump 16 and the insufflation pump 20, respectively, and provide bi-directional communication between the pumps and the controller 18 for the pressure and control signals.

During the procedure, the controller 18 actively controls the insufflation pump 20 and the valve pump 16 to maintain sufficient insufflation pressure inside the body cavity 11. Insufflation pressure may drop due to, among other things, leaks in or around the insufflation needle 22, the tubes 24a, 24b, or in the openings 28a, 28b. Insufflation gas can also escape when the endoscope is removed, e.g., to clean off condensation or body fluids. The controller 18 can control the valves to allow insufflation gas to escape from the body cavity 11.

Figure 4:
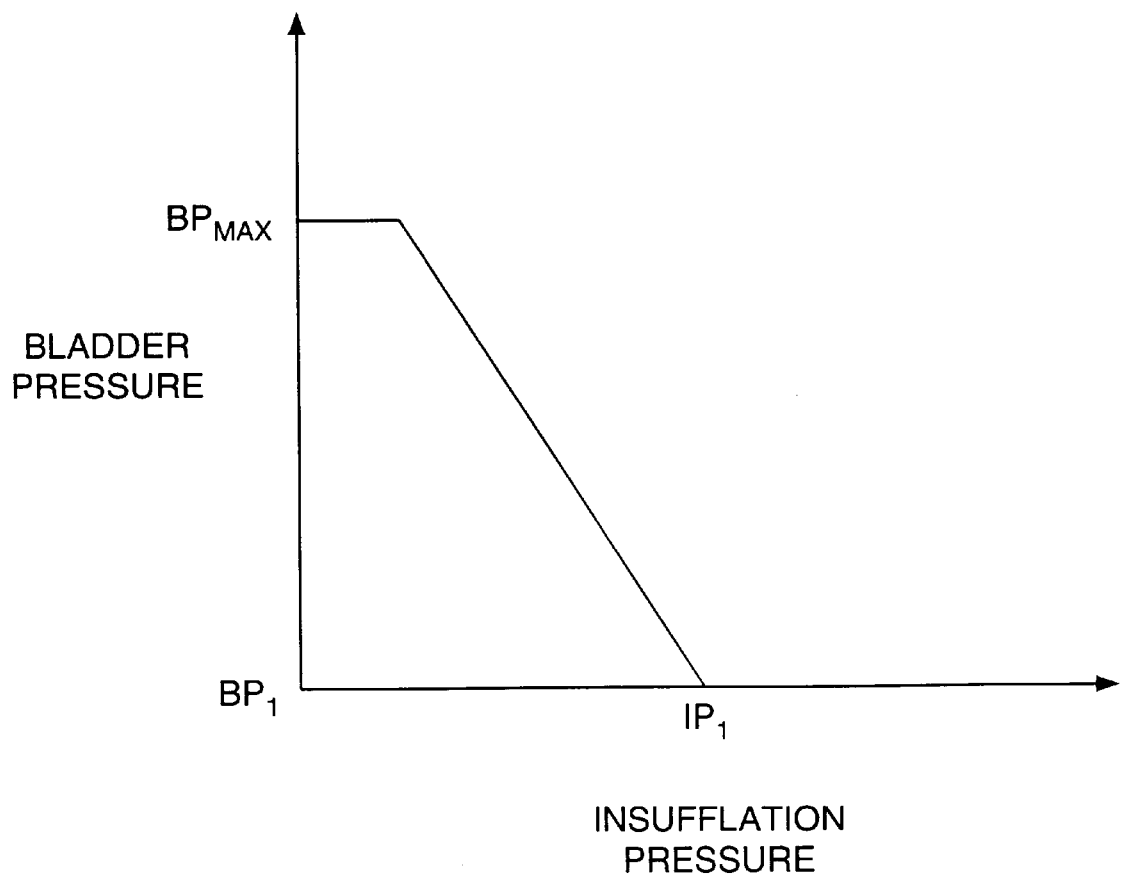
FIG. 4 is a graph showing bladder pressure versus insufflation pressure.

Referring to FIG. 4, when the insufflation pressure is at or above a desired insufflation pressure $IP_1$, the bladders in the valves are pressurized to $BP_1$, typically 1–2 mm Hg (0.04–0.08 in. Hg), with the valve pump 16 releasing gas from the bladder 23 as necessary. Should the insufflation pressure drop below $IP_1$, the controller 18 signals the valve pump 16 to pressurize the bladders and the insufflation pump 20 to pressurize the cavity. As the insufflation pressure drops below the desired pressure $IP_1$, the valve pump 16 linearly increases the bladder pressures until the maximum bladder pressure $BP_{max}$ is reached. Insufflation gas is supplied as necessary to the body cavity. The surgeon can also adjust the bladder pressure, e.g., so that he can more easily manipulate the implement.

Other embodiments are within the scope of the claims.

Figure 5:
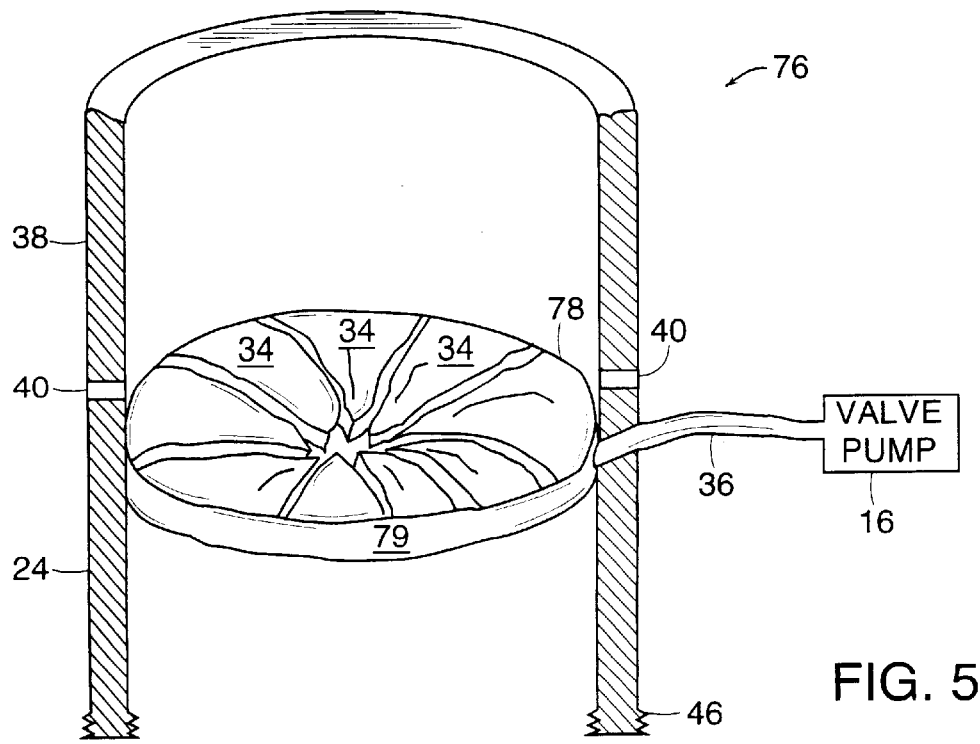
FIG. 5 is a partially cross-sectional view of another valve assembly for use in the system shown in FIG. 1.

For example, FIG. 5 shows an alternative valve assembly 76 including a sectional bladder 78 that has several triangular-shaped bladder segments or wedges 34. The bladder segments 34 may be fed by a single valve pump line 36 from the valve pump 16. Alternatively, the sectional bladder 78 may be a single piece with an undivided peripheral portion and a segmented central portion. Other bladder segment shapes could instead be used, such as rectangles or wedges with flattened or concave ends, as opposed to pointed ends. Also, the perimeter 79 of the sectional bladder 78 (or the perimeter 25 of the bladder 23) may be elliptical, rectangular, or square, with the inside surface 26 of the tube 24 having a similar shape.

The bladder 23 does not have to be annular. For example, the bladder can be a spherical balloon with no opening, carried on one side of the inner wall of the tube 24. As the bladder inflates, it presses the surgical implement against the opposite wall, and forms a seal around it.

Regardless of shape or configuration, the bladder 23 can be inflated with, and the valve pump 16 can supply, any fluid capable of pressurizing the bladder, such as a liquid (e.g., saline).

The tube 24 and sleeve coupling 40 can take a variety of forms. The tube 24 can be flexible or semi-rigid. All or part of the tube 24 can be pleated, giving the tube an accordion shape. The distal section of the tube 24 can include a threaded end 46 to be screwed into a mating coupling or other device (not shown) that seals to the patient 12 in or around the incision 13 (FIG. 1). The sleeve coupling 40 can be adapted to have the sleeve 38 clipped, snapped, or tied to the sleeve coupling 40.

The relationship between insufflation pressure and bladder pressure does not have to be the linear relationship shown in FIG. 4. For example, the bladder pressure could be a step response as a function of the insufflation pressure, rising quickly from $BP_1$ to the maximum bladder pressure when the insufflation pressure drops below $IP_1$.

Figure 6:
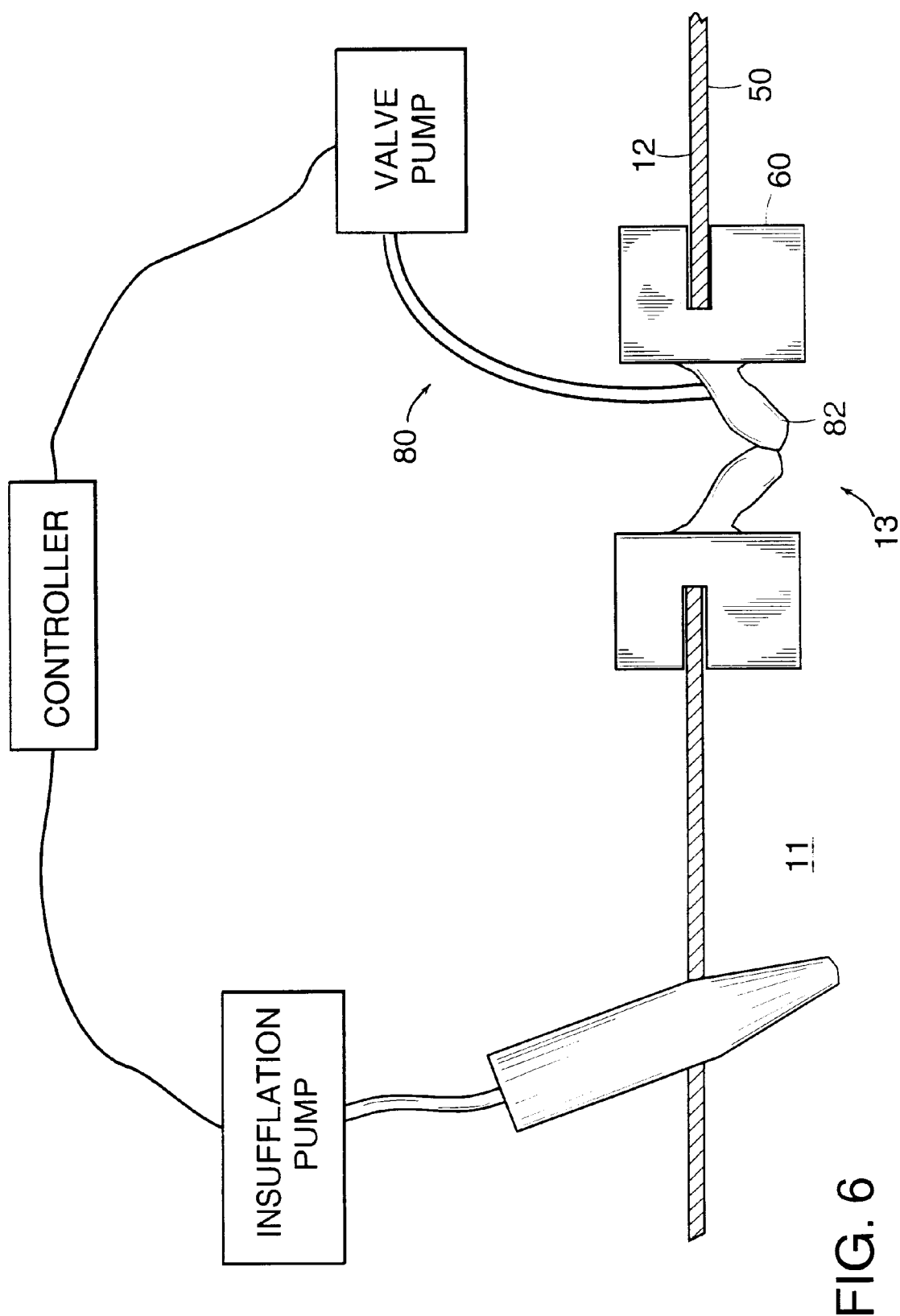
FIGS. 6–7 are partially cross-sectional detail views of insufflation systems.

FIG. 6 illustrates another embodiment of a valve assembly 80 that can be used at or near the incision 13. A sealing device 60 retracts the incision 13 and supports a bladder 82, which can be similar to the bladder 23 of FIG. 2 or the sectional bladder 78 of FIG. 5. The sealing device 60 can be an inflatable annular bladder, or can be rigid. The tube 24 (FIGS. 2, 5) can be configured to include the sealing device 60.

Figure 7:
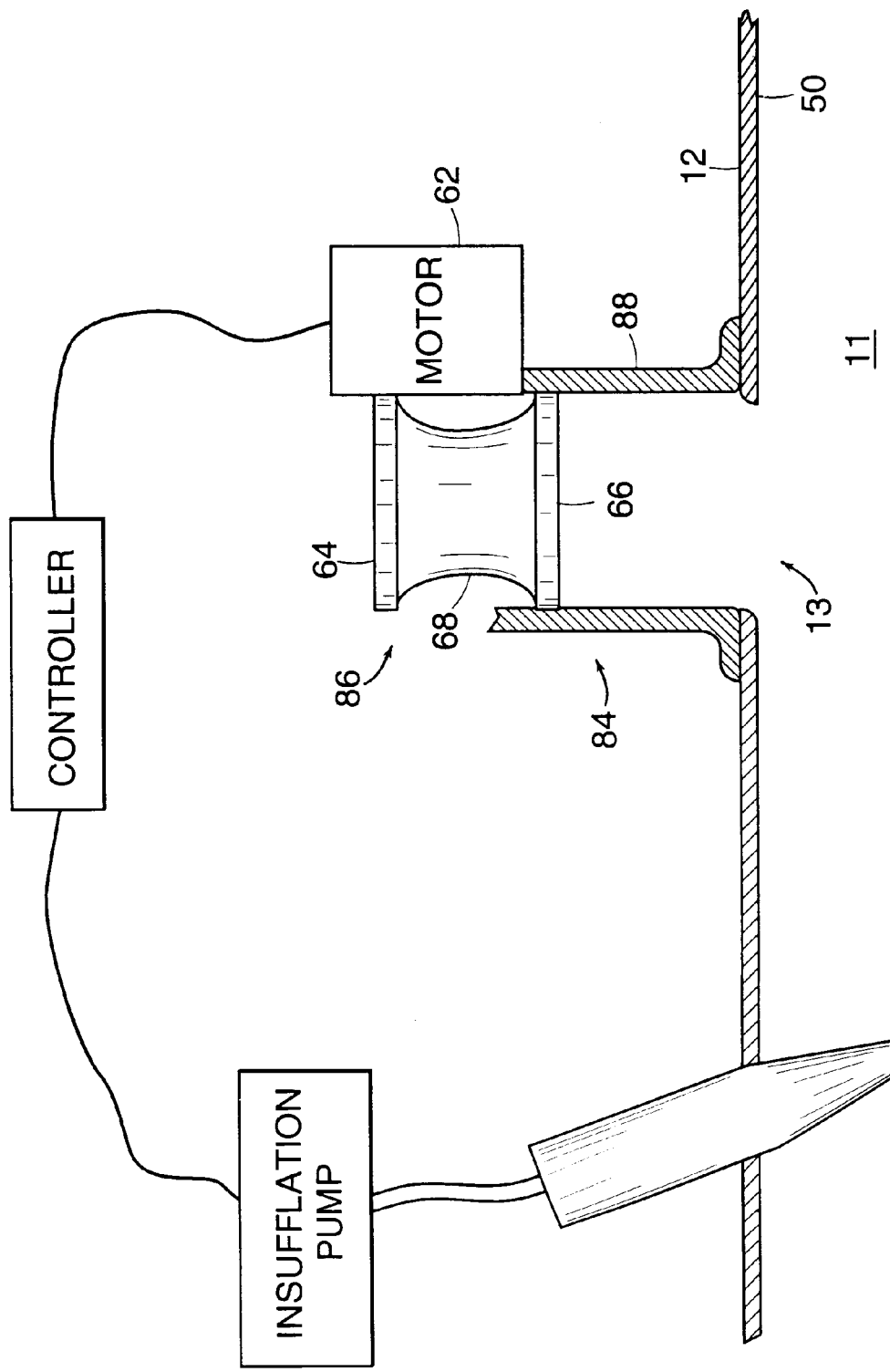

FIG. 7 illustrates another embodiment of a valve assembly 84, in which an iris shutter 86 can be used to close off a tube 88. A lower ring 66 is fixedly attached to the tube 88. A motor 62 actuates an upper ring 64 of the iris shutter 86, causing a flexible sheath 68 to twist and conform to the implement. While the iris shutter 86 is shown as being displaced a distance away from the patient 12, the iris shutter 86 may also be used at the level of the incision 13.

What is claimed is:

1. An apparatus for providing access to an opening in a body cavity containing insufflation gas at an insufflation pressure, the apparatus comprising:
    a controllable valve defining an access channel for a surgical implement and adapted to be coupled in fluid communication with the opening, the valve being responsive to an actuation signal to restrict flow of insufflation gas from the body cavity through the opening;
    a sensor for providing an output signal corresponding to the insufflation pressure; and
    a controller coupled to the controllable valve and the sensor and responsive to the output signal provided by the sensor to provide the actuation signal to the controllable valve.

2. The device of claim 1 wherein the controller produces the actuation signal if the output signal is indicative of an insufflation pressure below a desired insufflation pressure.

3. The device of claim 1 wherein the controllable valve comprises an iris valve.

4. The device of claim 1 wherein the output signal is electrical.

5. The device of claim 1 wherein the valve is adapted to conform to a periphery of the surgical implement.

6. The apparatus of claim 1 further comprising second controllable valve defining an access channel for a surgical implement and adapted to be coupled in fluid communication with the opening and to be responsive to an actuation signal to restrict flow of insufflation gas from the body cavity through the opening, the second controllable valve being for replacement of the first-mentioned controllable valve in the apparatus.

7. An apparatus for providing access to an opening in a body cavity containing insufflation gas at an insufflation pressure, the apparatus comprising:
    a controllable valve comprising an inflatable bladder and defining an access channel adapted to be coupled in fluid communication with the opening, the valve being responsive to an actuation signal to restrict flow of insufflation gas from the body cavity through the opening;
    a sensor for providing an output signal corresponding to the insufflation pressure; and
    a controller coupled to the controllable valve and the sensor and responsive to the output signal provided by the sensor to provide the actuation signal to the controllable valve.

8. The device of claim 7 wherein the inflatable bladder is annular.

9. The device of claim 8 wherein the inflatable annular bladder has a conical shape.

10. The device of claim 8 wherein the inflatable annular bladder is segmented.

11. The device of claim 8 wherein the annular bladder is sized to fit within the opening.

12. A system for providing access to an opening in an area of a body cavity containing insufflation gas at an insufflation pressure, the apparatus comprising:
    an inflatable annular bladder defining a chamber and a bladder opening through which the body opening can be accessed;
    a first source of pressurized gas in selective fluid communication with the chamber;
    an insufflation pressure sensor for providing an output signal corresponding to the insufflation pressure; and
    a controller coupled to the first source and to the insufflation pressure sensor and responsive to the output signal provided by the insufflation pressure sensor to provide a first control signal to the first source to control the first source to provide pressurized gas to the chamber.

13. The system of claim 12 wherein the controller provides the first control signal if the output signal indicates an insufflation pressure below a predetermined insufflation pressure.

14. The system of claim 12 wherein the controller does not provide the first control signal if the output signal indicate an insufflation pressure above a predetermined pressure.

15. The system of claim 12 further comprising a second source of pressurized gas coupled to the controller and adapted to selectively provide pressurized gas to the body cavity, wherein the controller is responsive to the output signal provided by the insufflation pressure sensor to provide a second control signal to the second source to control the second source to provide pressurized gas to the body cavity if the output signal indicates an insufflation pressure below a predetermined insufflation pressure.

16. The system of claim 12 further comprising a second source of pressurized gas coupled to the controller and adapted to selectively provide pressurized gas to the body cavity, wherein the controller is responsive to the output signal provided by the insufflation pressure sensor to provide a second control signal to control the second source not to provide pressurized gas to the body cavity if the output signal indicates an insufflation pressure above a predetermined insufflation pressure.

17. The system of claim 12 further comprising:

a chamber pressure sensor coupled to the bladder for providing a chamber pressure signal corresponding to a pressure in the chamber of the bladder;

an indicator coupled to the chamber pressure sensor and the insufflation pressure sensor responsive to the output signal of the insufflation pressure sensor and to the chamber pressure signal for providing an indication that the chamber pressure has reached a predetermined chamber pressure while the insufflation pressure is below a predetermined insufflation pressure.

* * * * *